(12) United States Patent
Winters

(10) Patent No.: US 6,464,706 B1
(45) Date of Patent: *Oct. 15, 2002

(54) TISSUE FIXATION DEVICE AND METHOD

(76) Inventor: Thomas F. Winters, 1800 Summerland Ave., Winter Park, FL (US) 32789

(*) Notice: Subject to any disclaimer, the term of this patent is extended or adjusted under 35 U.S.C. 154(b) by 16 days.

This patent is subject to a terminal disclaimer.

(21) Appl. No.: 09/638,370

(22) Filed: Aug. 15, 2000

Related U.S. Application Data

(63) Continuation-in-part of application No. 09/329,563, filed on Jun. 10, 1999, now Pat. No. 6,123,711.

(51) Int. Cl.[7] .............................................. A61B 17/56
(52) U.S. Cl. ...................................... 606/73; 623/13.14
(58) Field of Search ............................... 606/71, 72, 73, 606/104, 232; 623/13.11, 13.14

(56) References Cited

U.S. PATENT DOCUMENTS

| | | |
|---|---|---|
| 4,870,957 A | 10/1989 | Goble et al. |
| 4,988,351 A | 1/1991 | Paulos et al. |
| 5,013,316 A | 5/1991 | Goble et al. |
| 5,062,843 A | 11/1991 | Mahony, III |
| 5,108,431 A | 4/1992 | Mansat et al. |
| 5,129,902 A | 7/1992 | Goble et al. |
| 5,314,427 A | 5/1994 | Goble et al. |
| 5,352,229 A | 10/1994 | Goble et al. |
| 5,383,878 A | 1/1995 | Roger et al. |
| 5,403,136 A | 4/1995 | Mathys |
| 5,425,767 A | 6/1995 | Steininger et al. |
| 5,454,811 A | 10/1995 | Huebner |
| 5,571,184 A | 11/1996 | DeSatnick |
| 5,575,819 A | 11/1996 | Amis |
| 5,601,558 A | 2/1997 | Torrie et al. |
| 5,632,748 A | 5/1997 | Beck, Jr. et al. |
| 5,702,398 A | 12/1997 | Tarabishy |
| 5,718,706 A | 2/1998 | Roger |
| 5,766,250 A | 6/1998 | Chevitz et al. |
| 5,968,044 A * | 10/1999 | Nicholson et al. ............. 606/72 |
| 6,027,523 A * | 2/2000 | Schmieding ................. 606/232 |
| 6,093,201 A * | 7/2000 | Cooper et al. .............. 606/232 |
| 6,117,139 A * | 9/2000 | Shino .......................... 606/86 |
| 6,123,711 A * | 9/2000 | Winters ....................... 606/73 |

FOREIGN PATENT DOCUMENTS

| | | |
|---|---|---|
| EP | 0 232 049 A1 | 8/1987 |
| EP | 0 317 406 A1 | 5/1989 |

* cited by examiner

*Primary Examiner*—Eduardo C. Robert
(74) *Attorney, Agent, or Firm*—Allen, Dyer, Doppelt, Milbrath & Gilchrist, P.A.

(57) ABSTRACT

A system for fixing soft tissue within a bone tunnel includes a first fixation member that is adapted for insertion against a piece of soft tissue positioned within a bone tunnel, with a portion of the soft tissue emerging therefrom. The first fixation member has a proximal end and a distal end. A second fixation member can engage the first fixation member at its proximal end and also can prevent the first fixation member's proximal end from passing into the bone tunnel. The proximal end has barbs for engaging the soft tissue's second portion. Another element is engageable with the second fixation member for extracting it from engagement with the soft tissue's second portion.

20 Claims, 15 Drawing Sheets

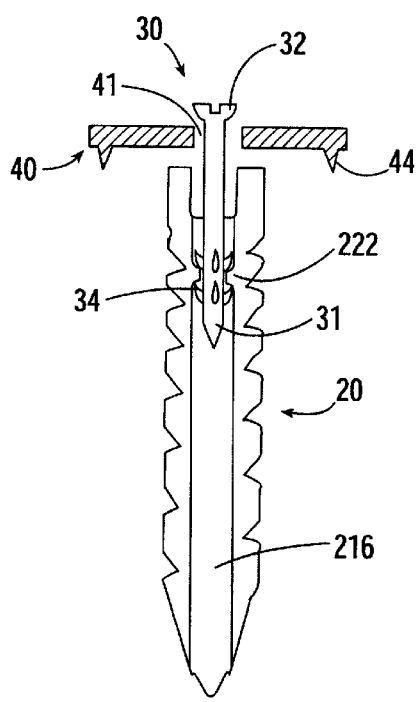
FIG. 3.
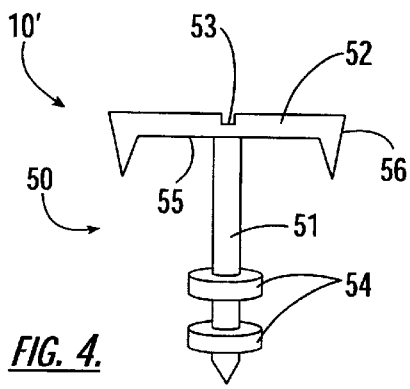
FIG. 4.
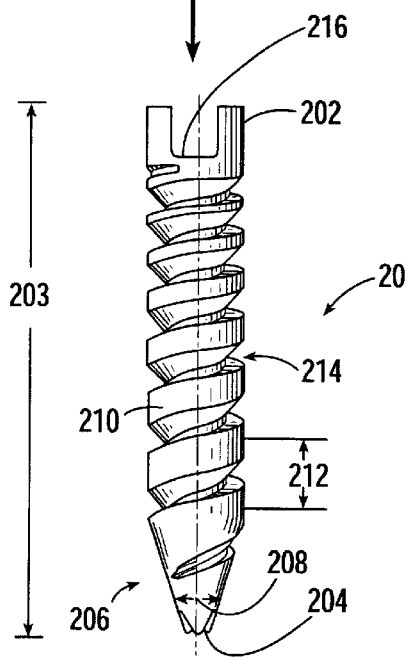
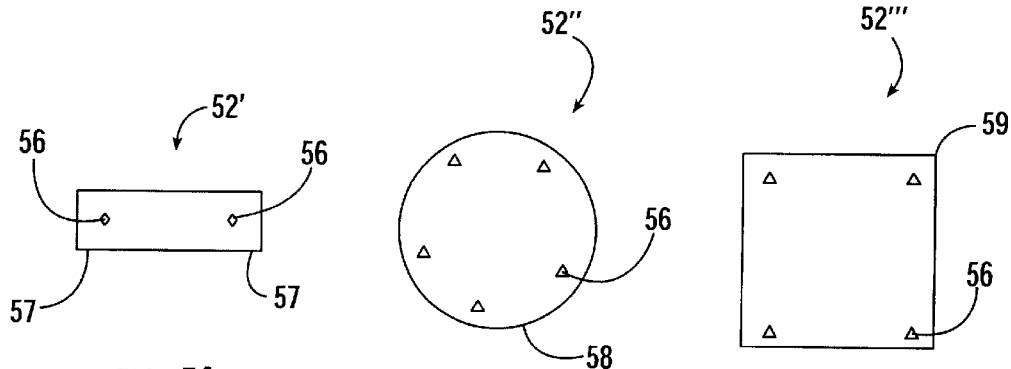
FIG. 5A.   FIG. 5B.   FIG. 5C.

TISSUE FIXATION DEVICE AND METHOD

CROSS-REFERENCE TO RELATED APPLICATION

This application is a continuation-in-part and claims priority to application Ser. No. 09/329,563, "Tissue Fixation Device and Method," filed Jun. 10, 1999, now U.S. Pat. No. 6,123,711.

BACKGROUND OF THE INVENTION

1. Field of the Invention

The present invention relates to surgical devices and methods for affixing two sections of tissue together, and, more particularly, to a device and method for affixing a piece of soft tissue to a bone or affixing two pieces of bone together.

2. Description of Related Art

Orthopedic surgical procedures sometimes require an attachment (or reattachment) of a flexible member to a bone. The flexible member might comprise soft tissue such as a ligament or tendon, a synthetic element, or suture. Devices and methods are known in the art to accomplish such an attachment, including those for affixing the flexible member within a hole of the bone.

For example, it is known to use a member such as a screw to press at least one end of the flexible member against the interior wall of a bone space (Mahony, U.S. Pat. No. 5,062,843; Roger et al., U.S. Pat. No. 5,383,878; Steininger et al., U.S. Pat. No. 5,425,767; Huebner, U.S. Pat. No. 5,454,811; Laboureau, EU 0 317 406). It is also known to anchor a ligament between two elements, the inner one deformable (U.S. Pat. No. 5,108,431), and to pass a ligament through a center of a device, creating tension by relative movement of elements (DeSatnick, U.S. Pat. No. 5,571,184).

A particular surgery in which flexible member attachment is required is endosteal fixation, wherein the terminal ends with bone plugs of an anterior cruciate ligament graft replacement material are attached within bone tunnels. The attachment is often achieved by compressive or interference fit means.

Other such surgeries include rotator cuff and SLAP lesion repairs.

In addition, it is known to affix two bone sections together, which at present is accomplished with bone screws and/or cabling.

Further, it is known to affix a section of soft tissue to a surface of a bone without the soft tissue proceeding into a bone tunnel (U.S. Pat. No. 4,988,351).

SUMMARY OF THE INVENTION

It is an object of the present invention to provide a system and method for affixing a piece of soft tissue to a bone.

It is a further object to provide such a system that has an element for securing the soft tissue piece within a bone tunnel and another element for securing another portion of the soft tissue against the outside the bone tunnel.

It is another object to provide such a system and method that permits repositioning the soft tissue following an initial fixation.

It is an additional object to provide a system and method for affixing two pieces of bone together.

These and other objects are attained with the system and method of the present invention. A particular embodiment of the system is for fixing soft tissue within a bone tunnel and comprises a first fixation member that has a proximal end and a distal end and is adapted for insertion upon a piece a first portion of soft tissue positioned within the bone tunnel. A second portion of the soft tissue is positioned to emerge from the bone tunnel. A second fixation member is adapted to engage the first fixation member at its proximal end. The second fixation member has means for restraining disengagement with the first fixation member and a proximal end, which has means for engaging the soft tissue's second portion. In an embodiment the first fixation member comprises a screw-type member having a bore extending from the proximal end and the second fixation member has a distal post portion adapted for mating with the bore and driving the screw rotationally thereby.

In a first subembodiment, the second fixation member comprises a tack member and a barbed washer that is rotatable about the post and retainable by a head portion on the tack member. The barbs on the washer are for engaging and restraining a movement of the soft tissue outside the bone tunnel.

In a second subembodiment, the second fixation member comprises a tack-type element that has a barbed head. As above, the barbs are for engaging and restraining the soft tissue outside the bone tunnel.

An alternate embodiment of the invention includes a system for affixing a piece of tissue to a bone, which may comprise affixing soft tissue to bone or two pieces of bone together. This system comprises a generally cylindrical cannula member that is adapted for insertion through the tissue piece and into a tunnel in the bone.

A generally cylindrical screw member is dimensioned for insertion through the cannula member, the screw member having a head at a proximal end and a bore extending at least partially therethrough from the proximal end. The bore has means for being driven by a driver.

A barbed washer has a hole extending from a proximal face through to a distal face. The hole is dimensioned for free rotation about the screw member and for retention by the screw head therebeneath. The distal face has a plurality of barbs extending generally distalward for engaging and retraining a movement of the distal tissue piece.

Yet another embodiment is also for a system for fixing soft tissue within a bone tunnel. The system comprises a first fixation member that has a proximal end and a distal end. The first fixation member is adapted for insertion against a first portion of soft tissue that has been positioned within a bone tunnel, with a second portion of the soft tissue emerging from the bone tunnel.

A second fixation member has means for engaging the first fixation member at its proximal end and also means for preventing the first fixation member's proximal end from passing into the bone tunnel. The proximal end has means for engaging the soft tissue's second portion.

Finally, means are engageable with the second fixation member for extracting it from engagement with the soft tissue's second portion.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 3 is a longitudinal cross-sectional view of the device of FIG. 1 illustrating the mating of the tack and the screw.

FIG. 4 illustrates a second embodiment of the fixation system having a barbed tack head.

FIGS. 5A–5C are axial cross-sectional views of different subembodiments of the tack head of FIG. 4.

(FIG. 6B) inserting the tack into the screw bore; and (FIG. 6C) impaling the soft tissue with the barbs outside the bone tunnel.

(FIG. 8B) delivering the screw to the bone tunnel and removing the cannula and permitting the barbs to bear against the soft tissue.

(FIG. 9B) delivering the screw to the second bone tunnel; and (FIG. 9C) removing the cannula and permitting the barbs to bear against the first bone.

(FIG. 12B) inserting a driver into the screw bore and driving the screw against the soft tissue in the bone tunnel and impaling the soft tissue with the barbs outside the bone tunnel; (FIG. 12C) if desired, pulling the washer and screw in a proximal direction to disengage them from the soft tissue using the suture looped around the washer; (FIG. 12B) repositioning the screw, washer, and soft tissue and removing the cannula.

DETAILED DESCRIPTION OF THE PREFERRED EMBODIMENTS

Figure 2A:
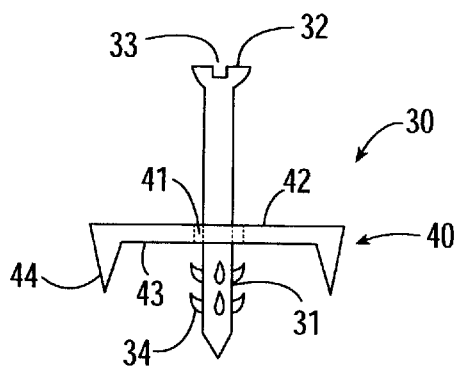
FIGS. 2A–2C are axial cross-sectional views of different subembodiments of the washer of FIG. 1.
Figure 2A:
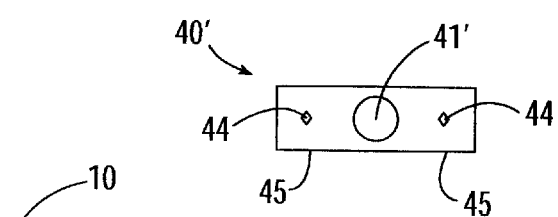
Figure 1:
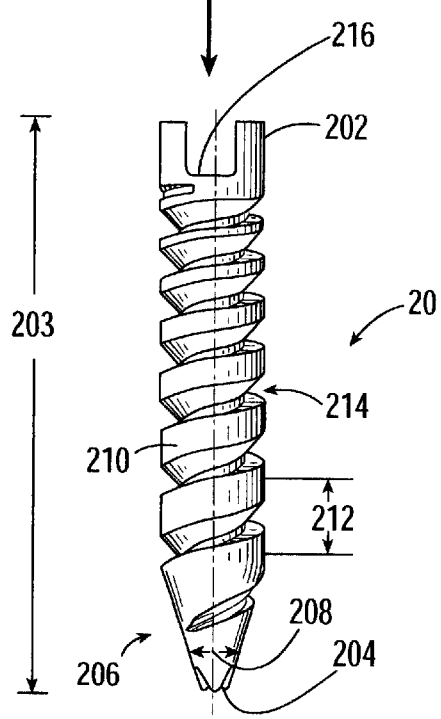
FIG. 1 illustrates a first embodiment of the fixation system having a barbed washer.
Figure 2B:
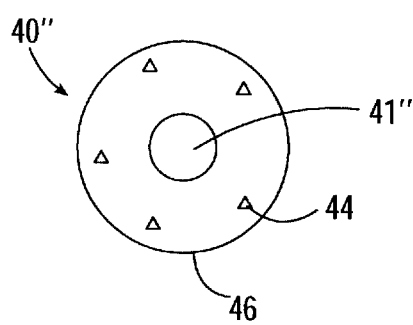
Figure 2C:
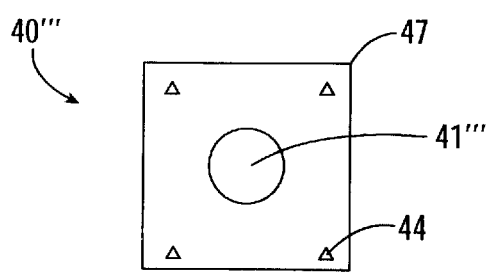

A description of the preferred embodiments of the present invention will now be presented with reference to FIGS. 1–12C.

An exemplary embodiment of the present invention comprises a system 10 including a first and a second fixation member and methods for affixing a piece of soft tissue ST within a bone tunnel BT in a patient. The first fixation member comprises a screw 20 such as has been previously disclosed in U.S. Pat. Nos. 5,503,634 and 5,730,744, the disclosures of which are incorporated herein by reference, although these particular embodiments are not intended as limitations.

The screw 20 has a proximal end 202, a distal end 204, and a length 203. Screw 20 further has a distal portion 206 having a narrowing cross section 208 toward distal end 204, in this specific embodiment the distal portion 206 forming a cone. Alternatively, a self-tapping distal portion could be implemented. In use an insertion of screw 20 into soft tissue is facilitated by the conical-shaped distal portion 206.

Along a central portion 214 between proximal end 202 and distal end 204, screw 20 has a variable-pitch helical protrusion 210. The helical pitch 212 along central portion 214 decreases from distal end 204 to proximal end 202. In use the decrease in helical pitch 212 serves to compress the soft tissue ST within the bone tunnel BT as screw 20 is advanced into the bone tunnel BT in a screwing motion.

The screw material in the preferred embodiment comprises a biodegradable plastic biocompatible with the soft tissue of the patient. Exemplary materials include a nontoxic blend of polycaprolactone and polyglycolide, a blend of polylactide and polyglycolide, pure polydioxanone, poly (ethylene oxide):poly(butylene terephthalate), polyorthoester, polyhydroxybutyrate, or cross-linked collagen. The material is designed to be sufficiently flexible and strong to withstand natural movement during healing. The material is also designed to be biodegradable within a first time span greater than or equal to a second time span over which the soft tissue ST can attach to the bone tunnel BT. In other words, the material is resorbed over a time span commensurate with the healing process, so that, once the soft tissue ST is attached, the screw 20 can gradually degrade, leaving an attached piece of soft tissue ST with no foreign material embedded therein.

In the preferred embodiment, screw 20 further has an axial bore 216. Bore 216 proceeds from proximal end 202 to distal end 204, and has a noncircular cross-sectional shape to permit an elongated post having a noncircular cross-sectional shape to pass into bore 216 and to advance screw 20 into the soft tissue ST by being rotated in a direction having a handedness commensurate with the helically shaped protrusion 210. The cross-sectional shape 220 may, for example, be triangular it or square, although these shapes are not intended as limitations.

Screw 20 further has a lip 222 projecting within the bore 216 for restraining barbs passing therebeyond (FIG. 3), as will be discussed in the following.

The second fixation member in a first embodiment comprises a tack 30 having a distal post portion 31 dimensioned for insertion into the screw's bore 216 and a proximal head portion 32 having a width greater than the width of the post portion 31. The tack's head 32 has means for being driven by a driver, such as an indentation 33 adapted for being driven by a driver having a commensurately shaped protrusion.

The tack 30 also has means for being restrained from disengagement with the screw's bore 216. In the embodiment shown in FIGS. 1 and 3, the restraining means comprises a protrusion extending outwardly from the post portion 31 engageable with the lip 222. In particular, the protrusion comprises a plurality of rows of generally proximally extending barbs 34. When at least one row of barbs 34 passes the lip 222 within the screw's bore 216, they are structurally restrained against proximal movement.

The second fixation member further comprises a barbed washer 40 that has a hole 41 extending from a proximal face 42 through to a distal face 43. The hole 41 is dimensioned for free rotation about the post 31 and thus is decoupled in at least one degree of freedom from the tack 30. The hole 41 is further dimensioned for retention by the tack's head portion 32 therebeneath. The distal face 43 has a plurality of barbs 44 extending generally distalward for engaging and retraining a movement of the soft tissue piece outside the bone tunnel BT.

Several embodiments of the washer 40 may be contemplated, although these are not intended as limitations: a generally rectangular shape 40' in axial cross section having two wings 45, a barb 44 extending from each wing (FIG. 2A); a generally circular shape 40" in axial cross section, the barbs 44 extending circumferentially about an edge 46 thereof (FIG. 2B); and a generally square shape 40''' in axial cross section, the barbs extending from adjacent each corner 47 thereof.

A second embodiment of the system 10' (FIGS. 4–5C) comprises a tack 50 having a distal post portion 51 dimensioned for insertion into the screw's bore 216 and a proximal head portion 52 having a width greater than the width of the post portion 51. The tack's head 52 has means for being driven by a driver, such as an indentation 53 adapted for being driven by a driver having a commensurately shaped protrusion.

The tack 50 also has means for being restrained from disengagement with the screw's bore 216. In the embodiment shown in FIG. 4, the restraining means comprises a protrusion extending outwardly from the post portion 51 engageable with the lip 222. In a particular embodiment, the protrusion comprises a plurality of generally annular deformable rings 54 that have sufficient flexibility to be pushed past the lip 222 but restrain removal in a proximal direction.

The tack's head 52 has a distal face 55 that has a plurality of barbs 56 extending generally distalward for engaging and retraining a movement of the soft tissue piece outside the bone tunnel BT.

Several embodiments of the head 52 may be contemplated, although these are not intended as limitations: a generally rectangular shape 52' in axial cross section having two wings 57, a barb 56 extending from each wing (FIG. 5A); a generally circular shape 52" in axial cross section, the barbs 56 extending circumferentially about an edge 58 thereof (FIG. 5B); and a generally rectilinear shape 52''' in axial cross section, the barbs 56 extending from adjacent each corner 59 thereof.

Figure 6A:
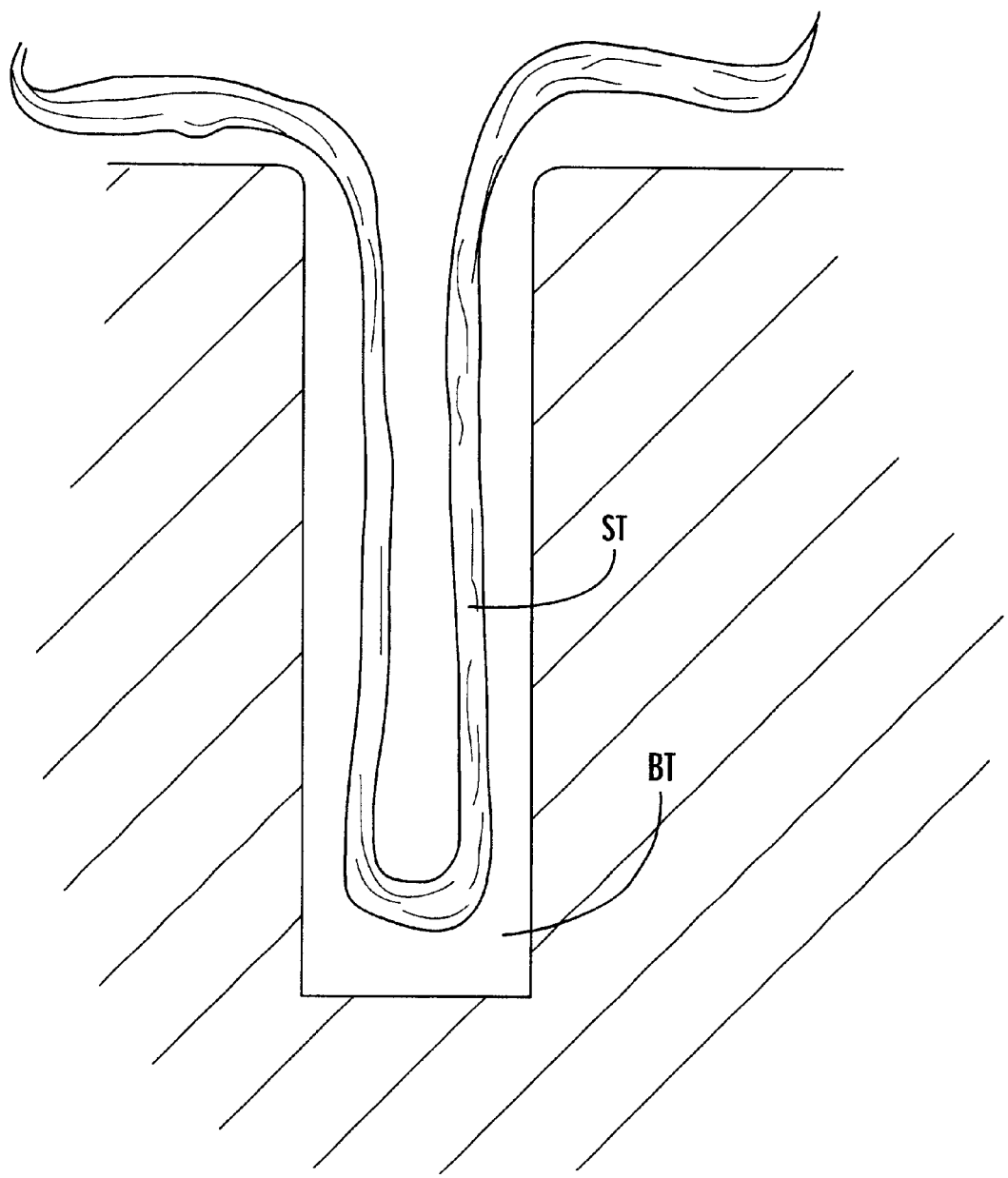
FIGS. 6A–6C illustrate an embodiment of the method of the present invention, including (FIG. 6A) inserting the screw into the bone tunnel atop a piece of soft tissue.
Figure 6B:
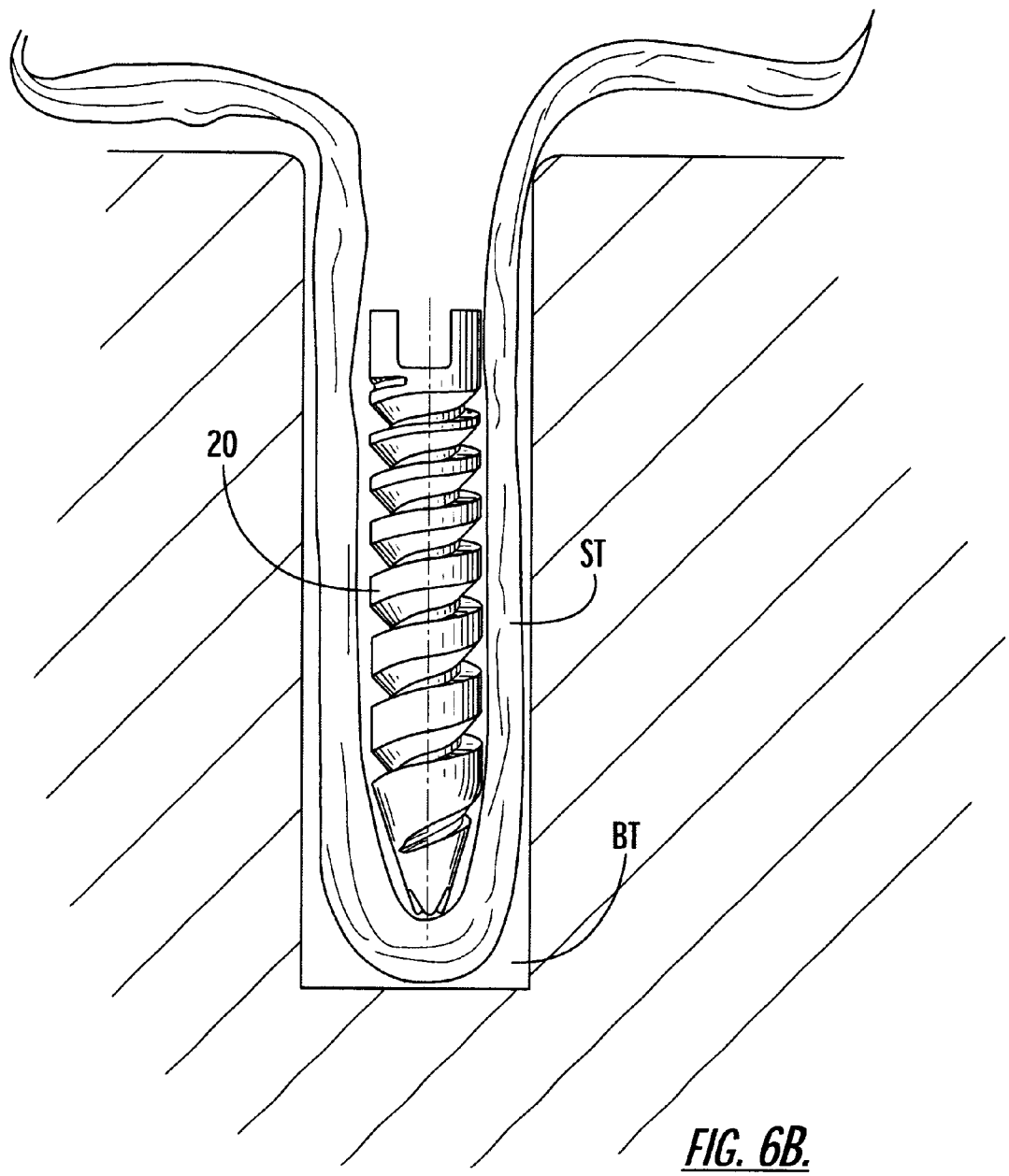
Figure 6C:
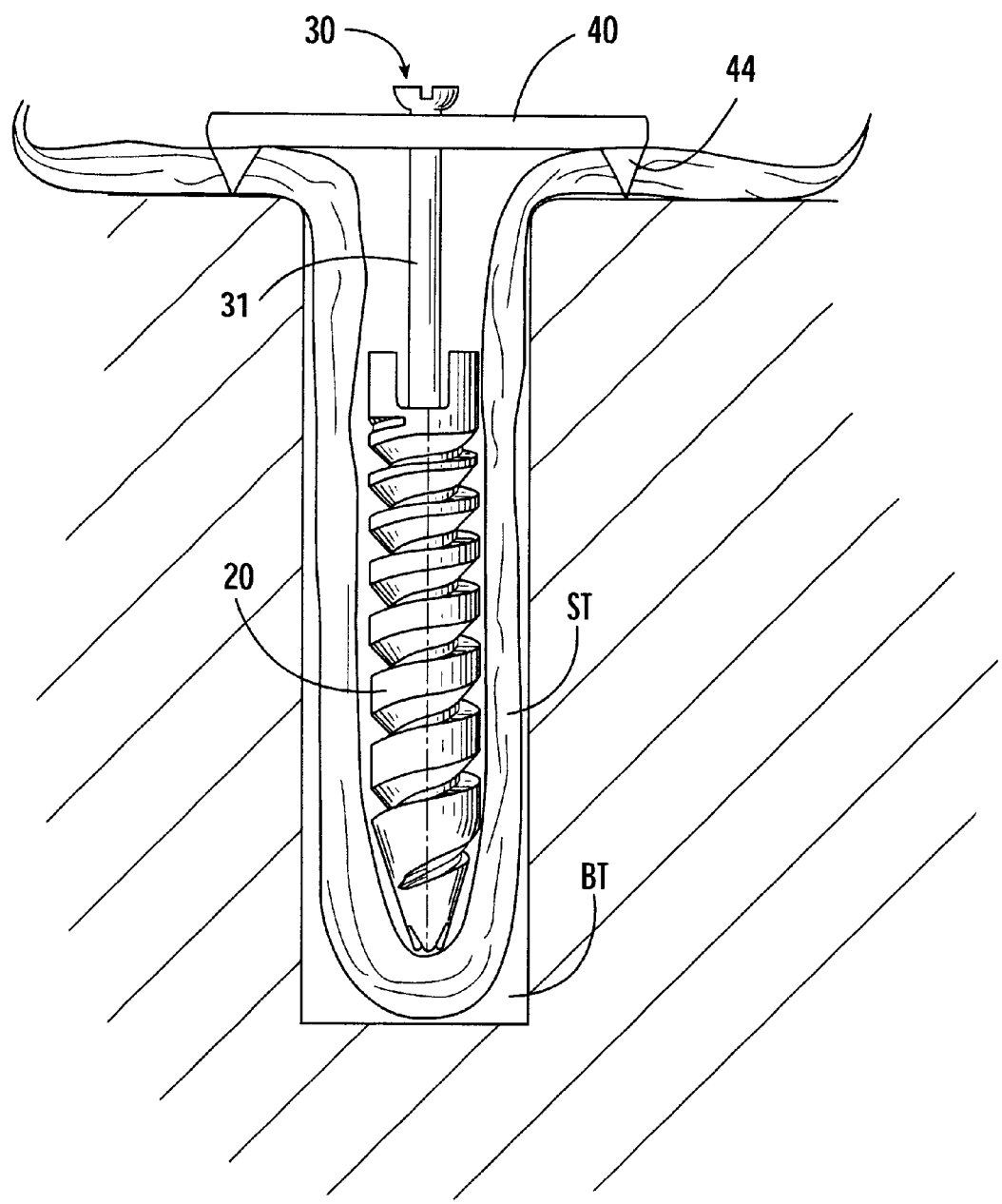

A method of using the devices (FIGS. 6A–C, shown for system 10) of the present invention to affix a piece of soft tissue ST within a bone tunnel BT comprises the step of positioning a piece of soft tissue ST so that a portion thereof resides within the bone tunnel BT. Next a first fixation member such as a screw 20 is positioned upon the piece of soft tissue ST within the bone tunnel BT (FIG. 6A), for example, using the cannula system described in U.S. Pat. Nos. 5,503,634 and 5,730,744 (not shown here).

The distal post portion 31 of the tack 30 is then engaged with a proximal portion of the screw 20, specifically, the post 31 is inserted into the screw's bore 216 until at least some of the barbs 34 pass the lip 222 and are restrained thereby from disengagement. In this embodiment the tack 30 is screwed into the screw's bore 216, while the washer 40 is permitted to spin with respect to the tack 30, thus avoiding engagement of the soft tissue ST by the washer's barbs 44 until desired.

A piece of the soft tissue ST outside the bone tunnel BT is then impaled upon the washer's barbs 44, which serves to provide additional fixation of the soft tissue ST.

A third embodiment of the system 60 (FIG. 7) is useful for affixing a piece of soft tissue ST within a bone tunnel BT or for affixing two pieces of bone B1,B2 together. The system 60 includes a cannula 62 that is adapted for insertion into the surgical site adjacent a bone tunnel BT. The cannula 62 is generally cylindrical and has a longitudinal bore 620 therethrough from a proximal end 621 to a distal end 622.

The screw 64, which is similar in construction to screw 20 above, is generally cylindrical and is dimensioned for insertion through the cannula 62. The screw 64 has a head 641 at a proximal end to 642, a threaded distal shaft portion 643, and a bore 644 extending at least partially therethrough from the proximal end 642. The bore 644 has a square shape for being driven by a commensurately shaped square driver D. Adjacent the head 641 is a reverse-threaded shaft portion 645.

A barbed washer 66 has a hole 662 extending from a proximal face 664 through to a distal face 666. The hole 662 is dimensioned for free rotation about the screw's shaft 643 and for retention by the screw head 641 therebeneath. The hole 662 also is reverse threaded for engaging the reverse-threaded portion 645 of the screw's shaft 643. The distal face 666 has a plurality of barbs 668 extending generally distalward for engaging and retraining a movement of the distal tissue piece ST or B1.

The washer 66 also has a flexible head that has a pair of outwardly extending wings 661, and the barbs 668 extend distal of each wing 661.

The screw 64 and washer 66 are dimensioned to pass through the cannula bore 620.

This embodiment 60 may be used either to affix soft tissue to bone or two pieces of bone together, as in the methods illustrated in FIGS. 8A–8B and 9A–9C. In the first, a piece of soft tissue ST is positioned with a first portion within a bone tunnel BT and a second portion extending therefrom. A cannula 62 is inserted into the surgical site with its distal end 628 positioned adjacent the bone tunnel BT and against the soft tissue's ST second portion (FIG. 7).

Figure 7:
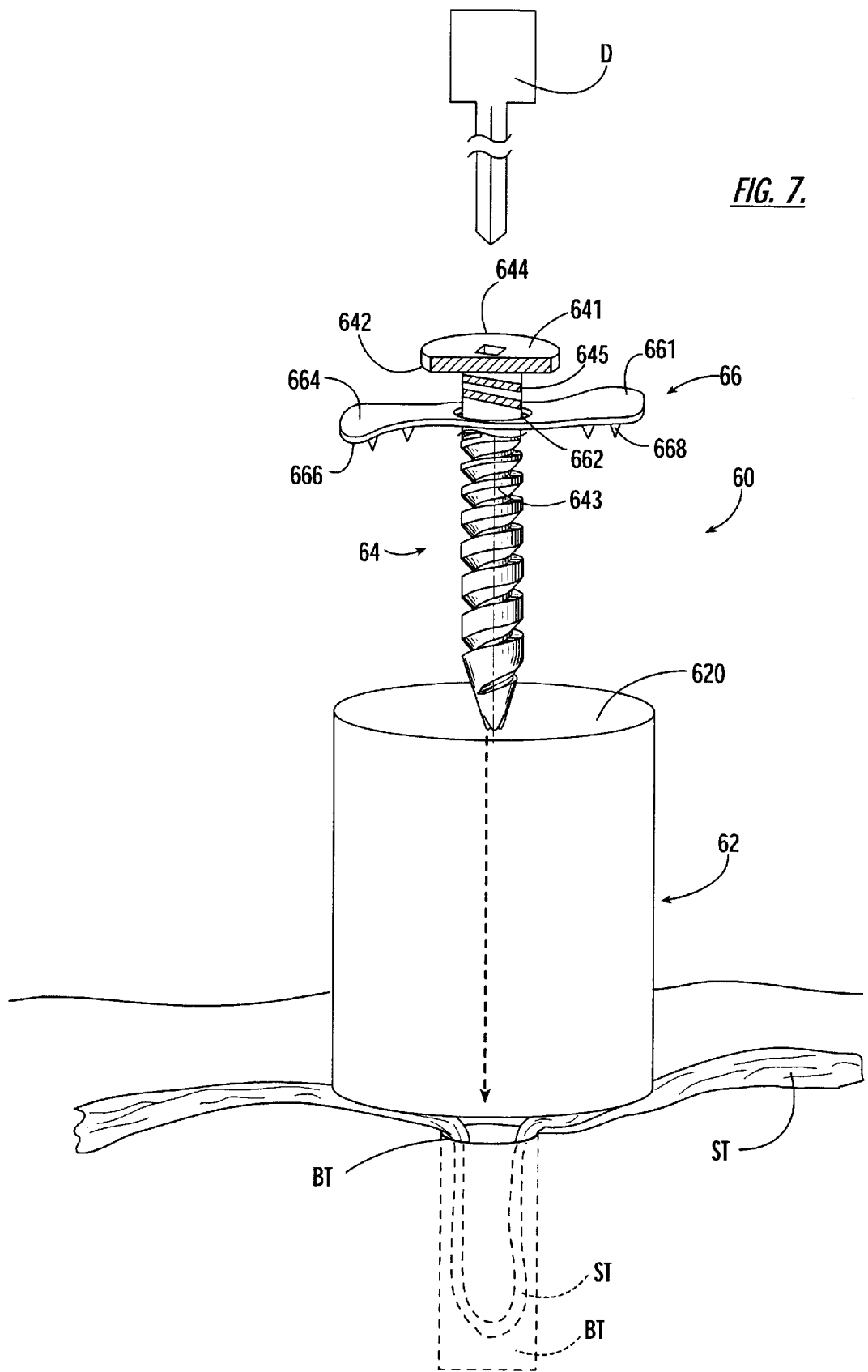
FIG. 7 illustrates an exploded view of a third embodiment of the system using a cannula for guiding the screw.
Figure 8A:
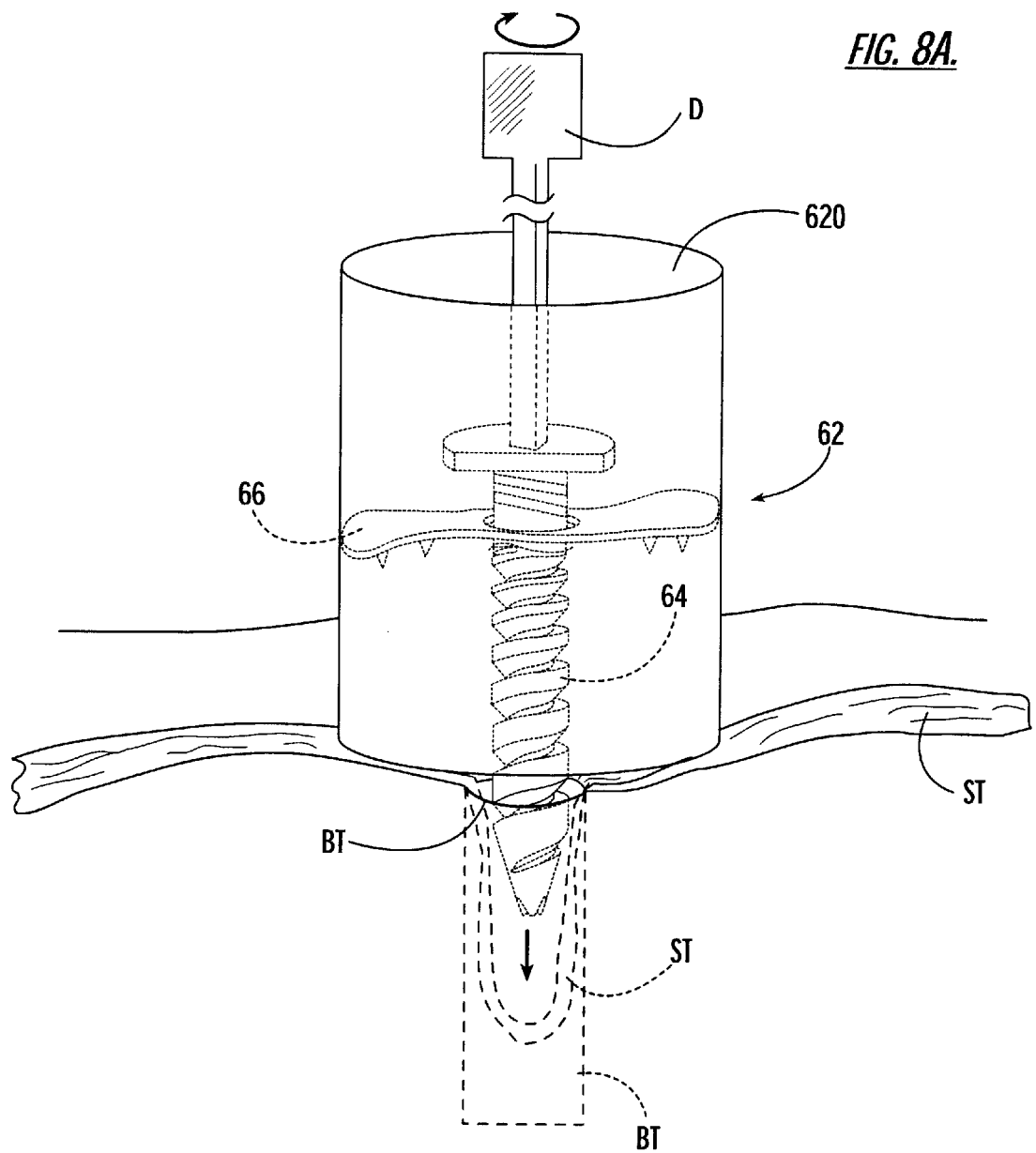
FIGS. 8A–8B illustrate the method of using the embodiment of FIG. 7 to affix soft tissue within a bone tunnel, including (FIG. 8A) inserting the cannula into the site and inserting the screw and washer into the cannula.

A screw 64 is inserted through the hole 662 in the washer 66, and the screw 64 and washer 66 assemblage is inserted into the cannula 62 (FIG. 7). The screw 64 is driven into the bone tunnel BT and against the soft tissue ST, with the washer 66 permitted to spin against the screw 64 while being retained within the cannula's proximal portion 622 (FIG. 8A).

Figure 8B:
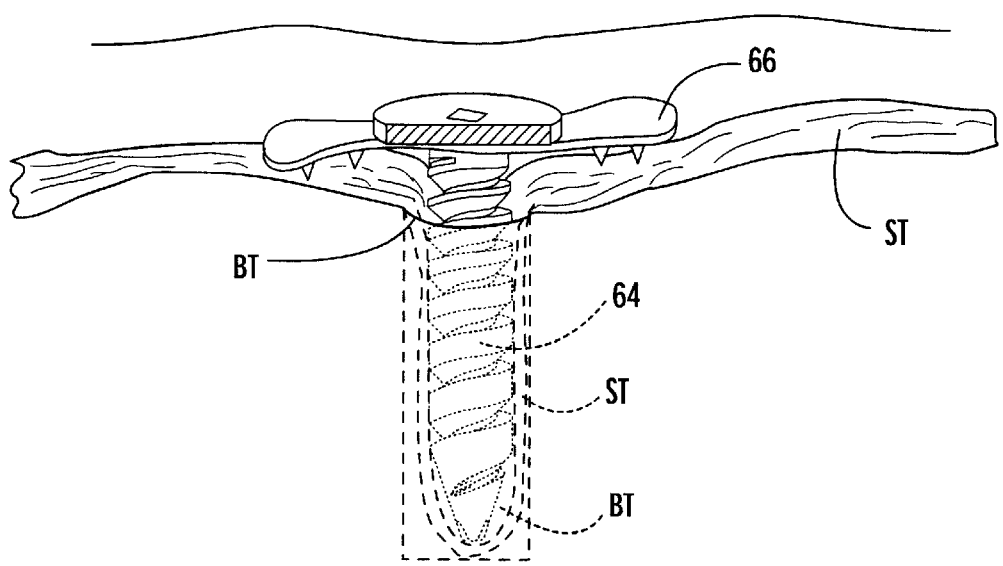

Next the cannula 62 is removed from the surgical site, and the barbs 663 are permitted to bear against the soft tissue's ST second portion adjacent the tunnel BT (FIG. 8B).

In the second method using the system 60, a distal B2 and a proximal B1 piece of bone are affixed together. This method comprises the steps of making a hole H through the proximal bone piece B1. Next a tunnel BT is made in the distal bone piece B2.

Figure 9A:
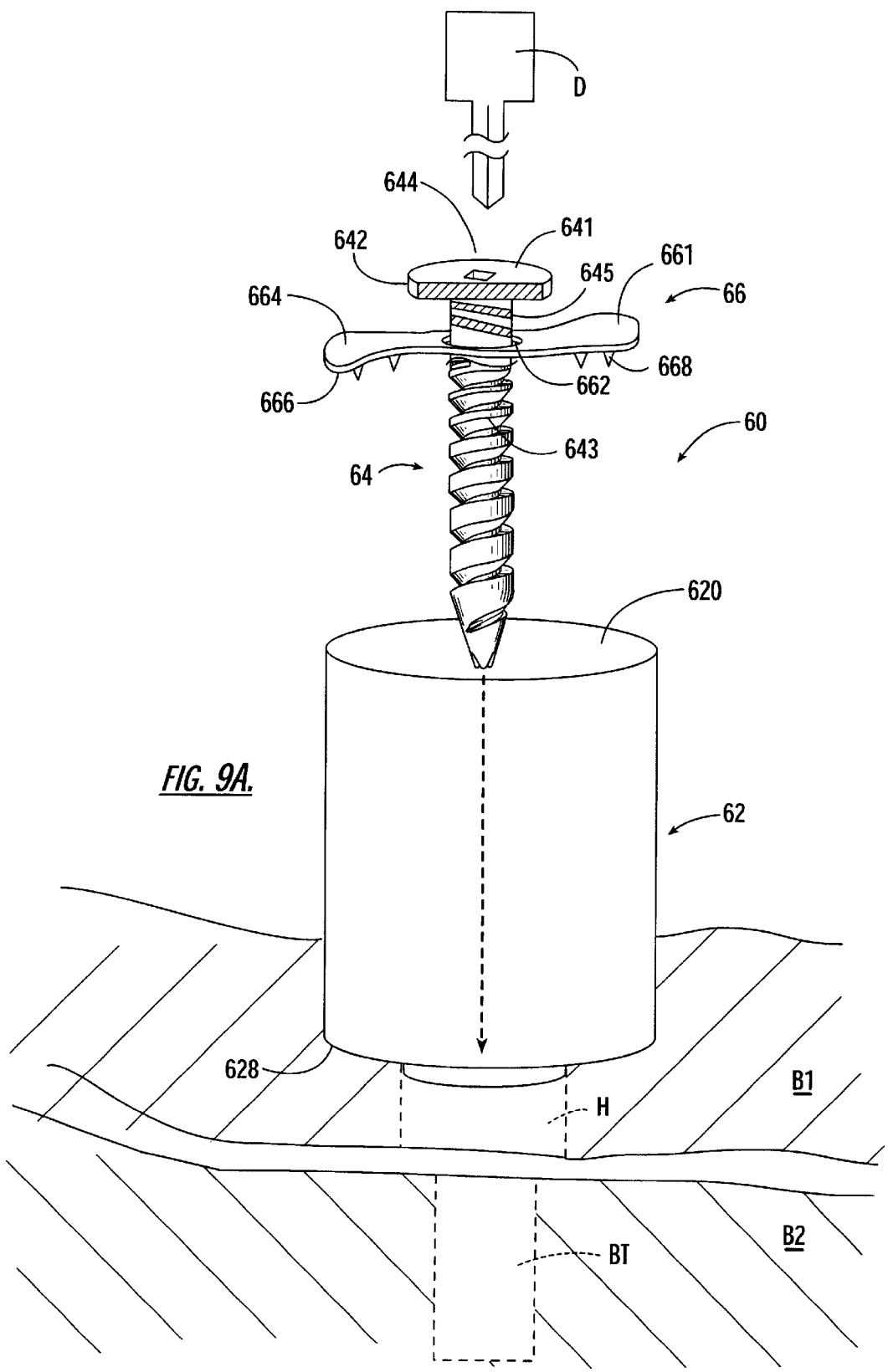
FIGS. 9A–9C illustrate the method of using the embodiment of FIG. 7 to affix two pieces of bone together, including (FIG. 9A) inserting the cannula into the first bone piece and inserting the screw and washer into the cannula.
Figure 9B:
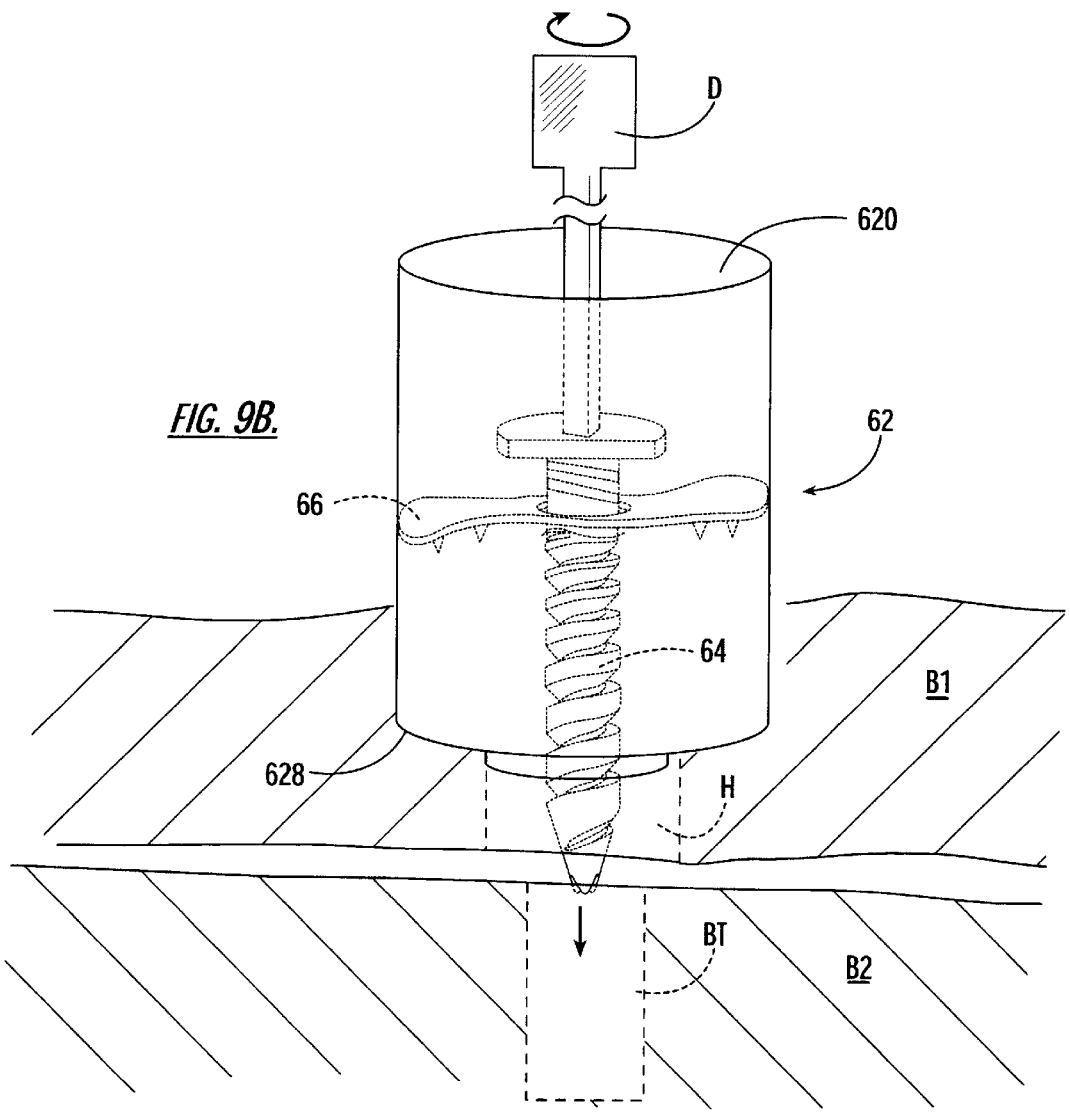

The cannula 62 is positioned with a distal end 628 adjacent the proximal bone piece hole H. A screw 64 and washer 66 assemblage is inserted into the cannula 62 (FIG. 9A). The screw 64 is driven into the distal bone piece tunnel BT, with the washer 66 permitted to spin against the screw 64 while being retained within the cannula's proximal portion 622 (FIG. 9B).

Figure 9C:
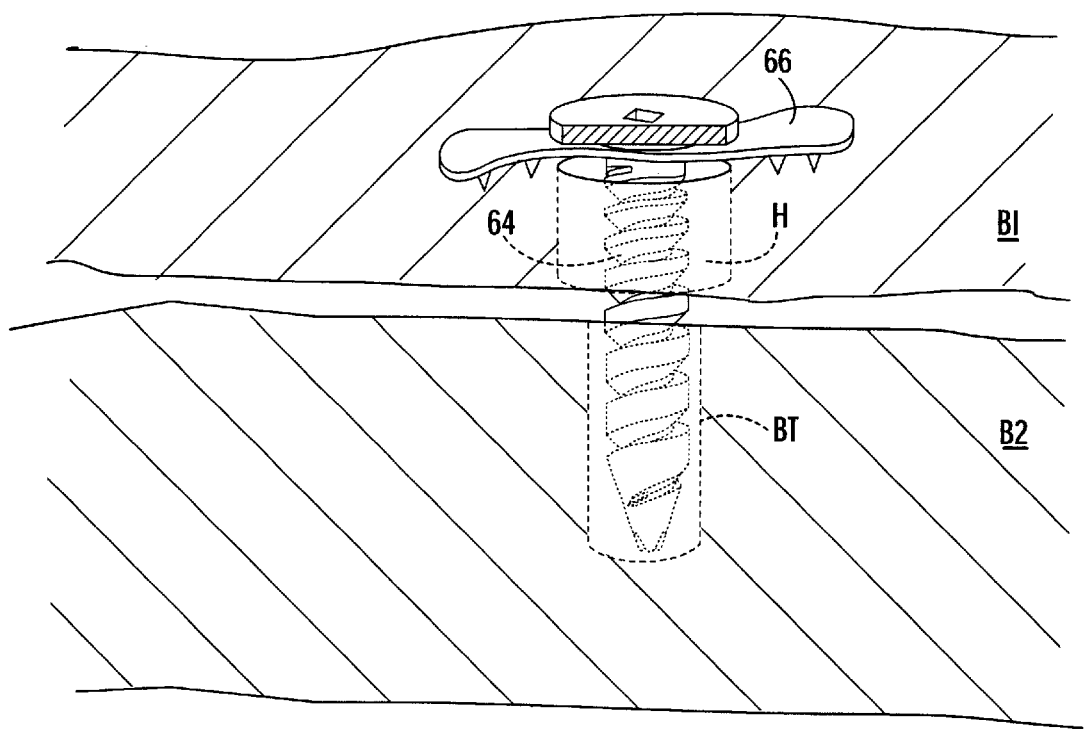

Then the cannula 62 is removed from the proximal bone piece hole H, and the barbs 663 are permitted to bear against the proximal bone portion B1 adjacent the hole H (FIG. 9C).

Figure 11:
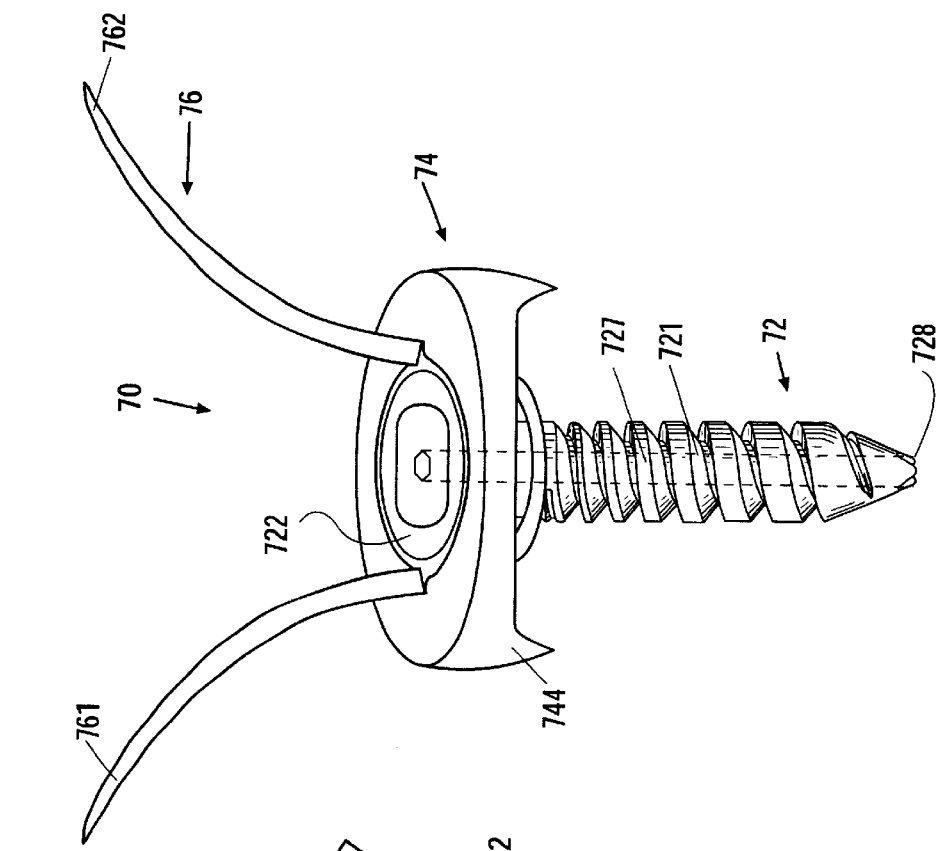
FIG. 11 is a top-side plan view of the assembled system of FIG. 10.
Figure 10:
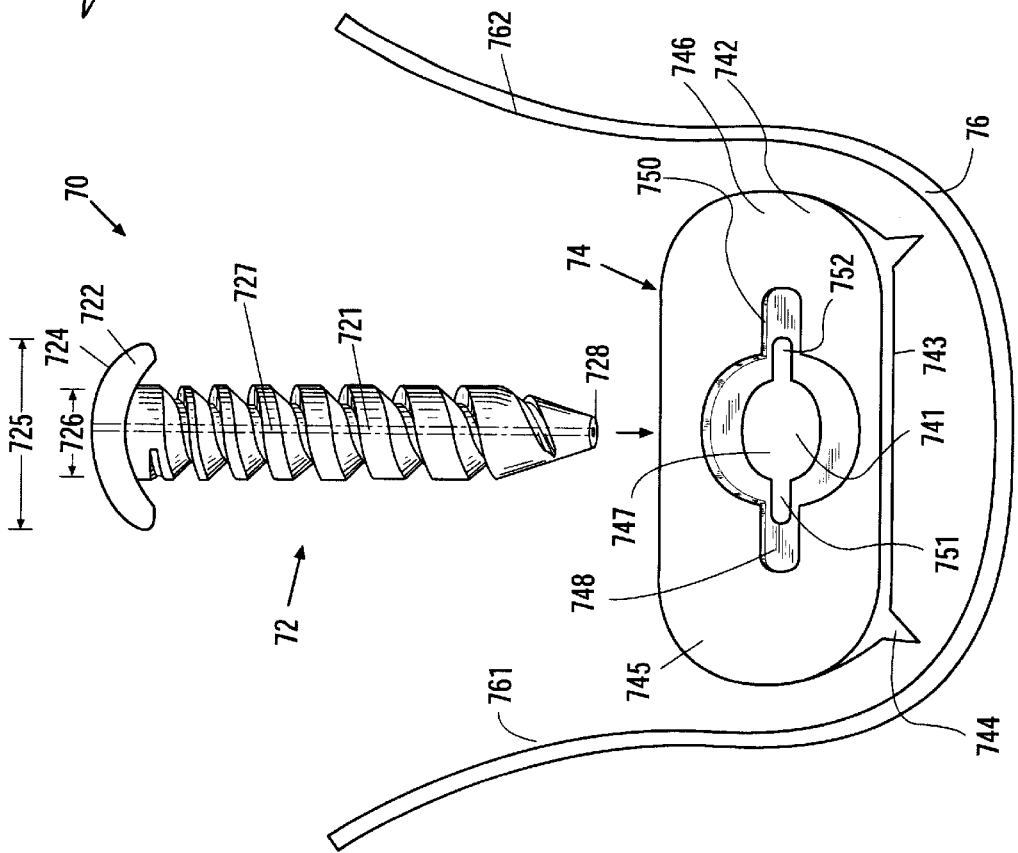
FIG. 10 is an exploded view of another embodiment of a system for fixing soft tissue within a bone tunnel. The screw and washer are shown in side perspective view, and the washer in top plan view.
Figure 12A:
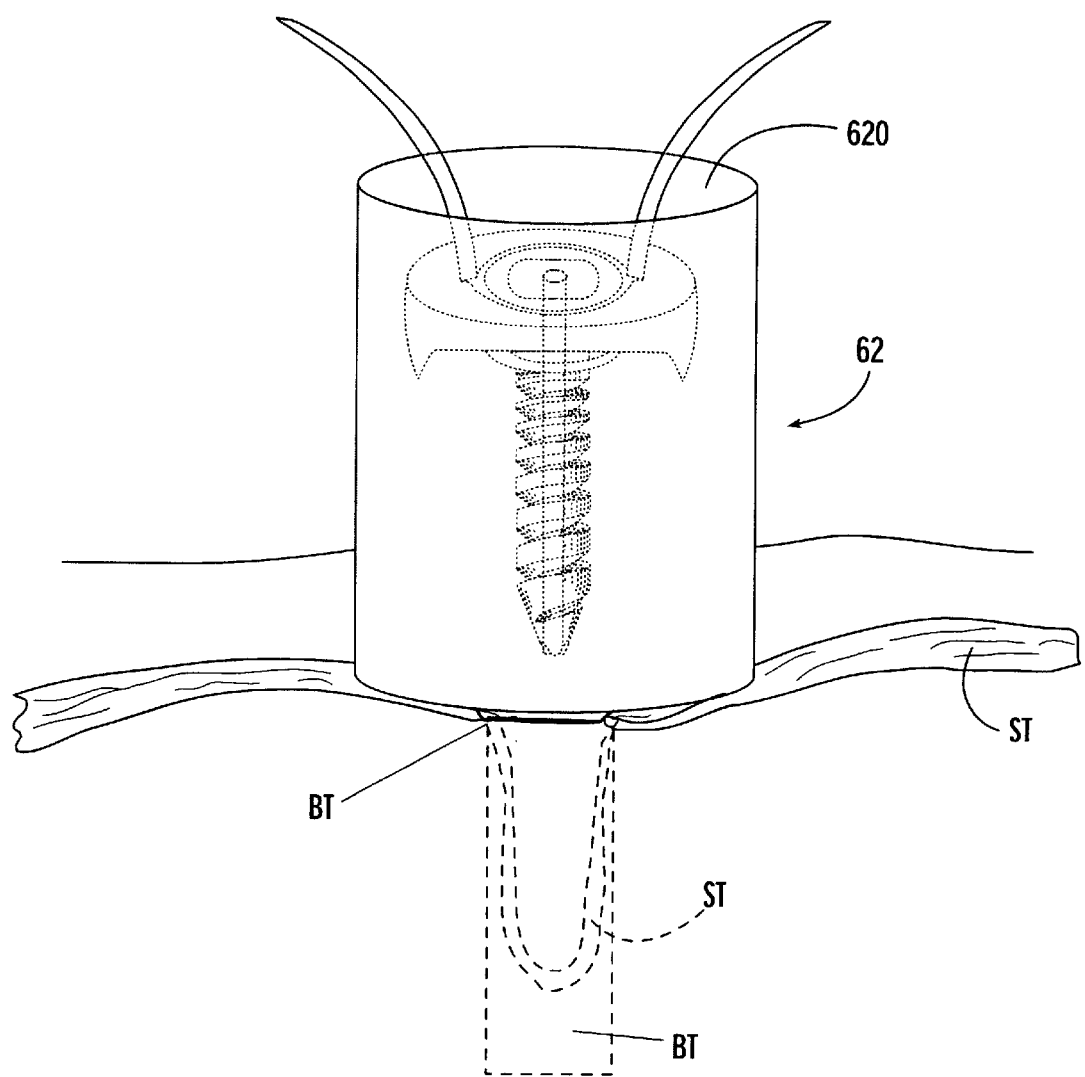
FIGS. 12A–12C illustrate another embodiment of the method of using the invention of FIG. 10, including (FIG. 12A) inserting the screw and washer through a cannula, the screw placed adjacent the bone tunnel.
Figure 12B:
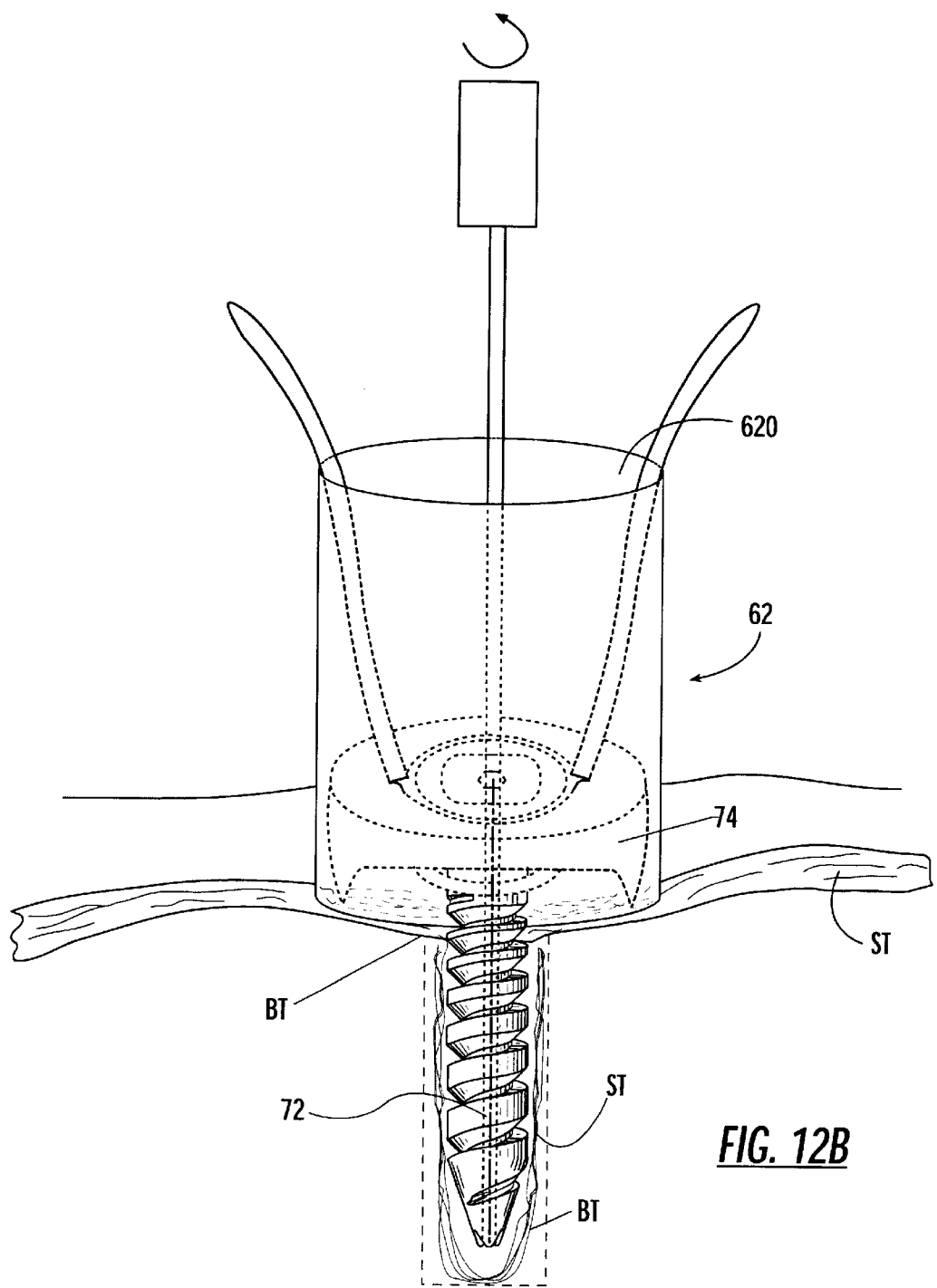
Figure 12C:
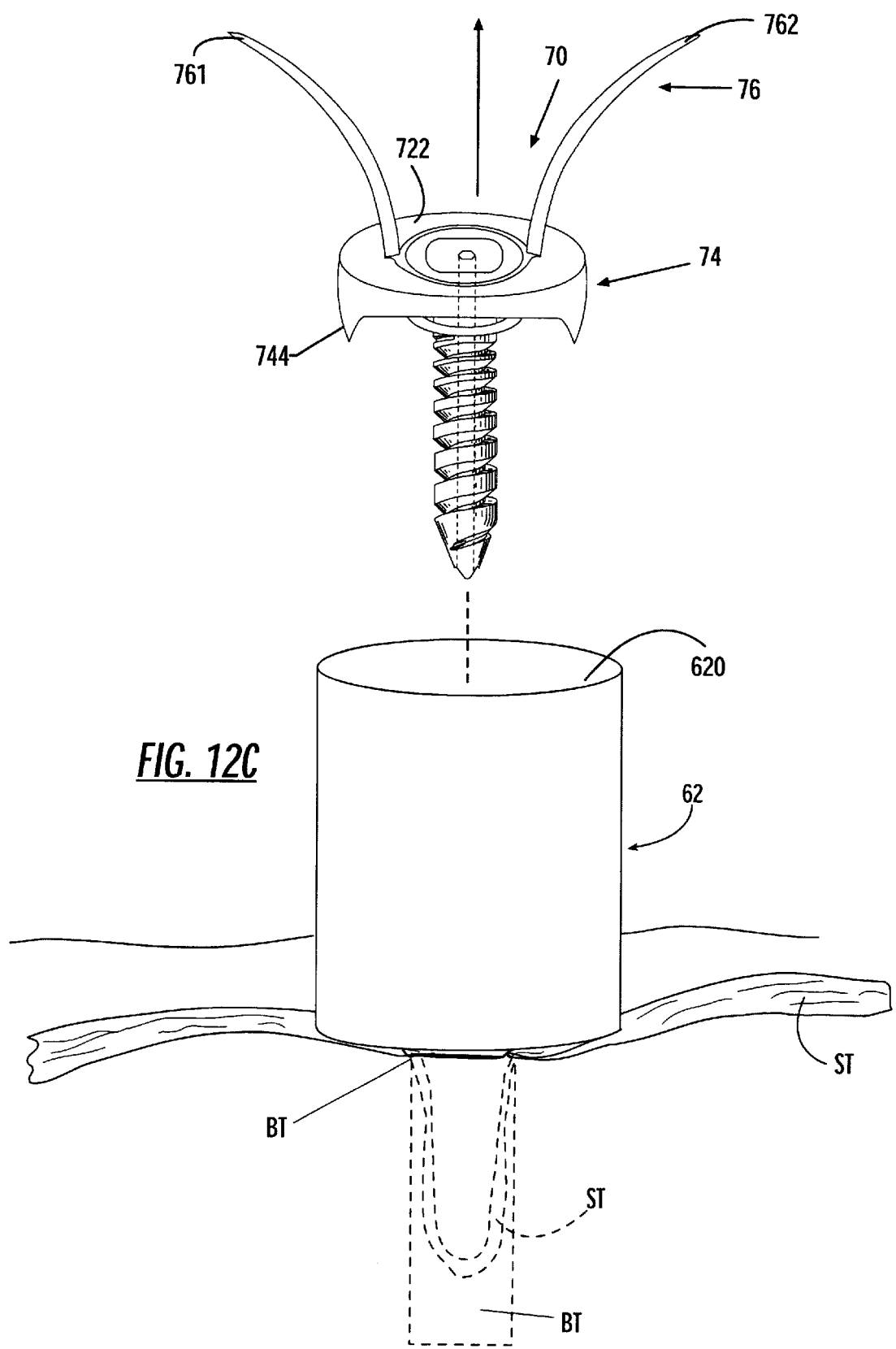

Yet another embodiment of the system 70 of the invention is illustrated in FIGS. 10 and 11, with the associated method illustrated in FIGS. 12A–12C. This system 70, again for fixing soft tissue ST within a bone tunnel BT.

Here the first fixation member again comprises a screw-type member. This screw 72 has a threaded distal portion 721 and a head 722 at the proximal end 724. The head 722 has a diameter 725 greater than the diameter 726 of the distal portion 721. The head 722 has a generally circular shape in axial cross section and means for being driven by a driver D.

In a preferred embodiment the screw 72 has an axial bore 727 that extends from the proximal end 724 and through to the distal end 728. The bore 727 is noncircular in axial cross section for permitting the driver D to pass into the bore 727 and to advance the screw 72 by being rotated in a direction having a handedness commensurate with the screw's threads 721.

The second fixation member in this embodiment comprises a barbed washer-type member. The washer 74 has a hole 741 that extends from a proximal face 742 through to a distal face 743. The hole 741 is dimensioned to engage the screw 72 by admitting the screw's distal portion 721. The hole 741 is further dimensioned to permit the screw 72 to turn therein in one degree of freedom, so that the screw 72 can be rotated without turning the washer 74.

The hole 741 is smaller than the screw's head 722, which serves to prevent the screw's proximal end 724 from passing distal of the washer's distal face 743 and into the bone tunnel BT when the screw 72 and washer 74 are engaged. The distal face 743 has a plurality of barbs 744, here 4, that extend generally distalward. As in previous embodiments, the barbs 744 are adapted to engage and restrain a movement of the soft tissue ST. In this embodiment the washer 74 has a generally oval shape in axial cross section that has two wings 745,746. A pair of barbs 744 extend from each wing 745,746.

The washer's hole 741 has a distal portion 747 that is smaller than the head 722 and a proximal portion 748 that is dimensioned to admit the head 722 thereinto. This permits a countersinking engagement, which permits the head's proximal face 724 to be substantially flush with the washer's proximal face 742 when the screw 72 and the washer 74 are engaged.

In a particular embodiment the engaging means comprises means for reversibly locking the screw 72 and the washer 74 together. This may be accomplished, for example, by positioning a flexible lip 750 within the washer's hole's proximal portion 748 that will permit the entry of the screw head 722 but resist, but not prevent, its removal.

A second 751 and a third 752 hole also extend through the washer 74 from the proximal face 742 to the distal face 743, and are in communication with and smaller than the first hole 741, although this is not intended as a limitation.

Finally, means are engageable with the washer 74 for extracting it from engagement with the soft tissue's ST second portion. In a particular embodiment the extracting means comprises an elongated flexible member, such as a wire or suture 76 that is engageable with the washer 74.

In this embodiment the second 751 and the third 752 holes are each dimensioned to permit the flexible member 76 to pass therethrough. The flexible member 76 in use has its first end 761 passed through the second hole 751 and its second end 762 passed through the third hole 752 so that both 761,762 emerge from the washer's proximal face 742. to create a noose therearound.

The method for using this system 70 to affix a piece of soft tissue ST within a bone tunnel BT is illustrated in FIGS. 12A–12C and comprises the steps of positioning a piece of soft tissue ST so that a portion thereof resides within a bone tunnel BT. A cannula 62 is inserted into a surgical site with a distal end 628 positioned adjacent the bone tunnel BT and against the soft tissue's ST second portion (FIG. 12A).

The screw 72 and washer 74 are engaged, with the screw's threaded portion 721 passed through the washer's first hole 741. This assemblage 72,74 is passed through the cannula 62, and the screw 72 is positioned against the piece of soft tissue ST within the bone tunnel BT with a screwing motion using a driver D (FIG. 12B). The barbs on the washer 74 are then permitted to engage a piece of the soft tissue ST outside the bone tunnel BT.

If desired, the washer 74 may be disengaged from the soft tissue ST piece and repositioned against a different part of the soft tissue ST outside the bone tunnel BT. In addition, if desired, the screw 72 may be disengaged from the soft tissue ST piece within the bone tunnel BT, so that the soft tissue ST and the screw 72 may be repositioned.

These repositioning steps are accomplished by attaching a flexible member 76 to the washer 74 as described above and pulling the flexible member 76 until the barbs 744 are removed from the soft tissue ST piece (FIG. 12C). Finally, when the assemblage 72,74 and the soft tissue ST are positioned as desired, the cannula 68 is removed from the surgical site.

It may be appreciated by one skilled in the art that additional embodiments may be contemplated, including screws, systems, and methods for affixing other flexible members into tunnels, such as in the artificial ligaments and tendons and suture.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A system for fixing soft tissue within a bone tunnel comprising:
   a first fixation member having a proximal end and a distal end and adapted for insertion against a first portion of soft tissue positioned within a bone tunnel, a second portion of the soft tissue emerging from the bone tunnel;
   a second fixation member having:
      means for engaging the first fixation member at the proximal end thereof;
      means for preventing the first fixation member proximal end from passing into the bone tunnel; and
      a distal face having means for engaging the soft tissue second portion; and
   means engageable with the second fixation member for extracting the second fixation member from engagement with the soft tissue second portion.

2. The system recited in claim 1, wherein the preventing means comprises means for preventing the first fixation member proximal end from passing distal of a distal face of the second fixation member.

3. The system recited in claim 1, wherein the second fixation member when engaged with the first fixation member is decoupled in at least one degree of freedom therefrom.

4. The system recited in claim 1, wherein the first fixation member comprises a screw-type member having a threaded distal portion and a head at the proximal end, the head having a diameter greater than a diameter of the distal portion.

5. The system recited in claim 4, wherein the second fixation member engaging means comprises a barbed washer-type member having a hole extending from a proximal face through to the distal face, the hole dimensioned to admit the screw-type member distal portion and smaller than the screw-type member head portion, the distal face engaging means comprising a plurality of barbs extending generally distalward for engaging and restraining a movement of the soft tissue piece.

6. The system recited in claim 5, wherein the screw-type member head has means for being driven by a driver.

7. The system recited in claim 5, wherein the washer-type member hole has a distal portion smaller than the screw-type member head and a proximal portion dimensioned to admit the screw-type member head thereinto, for permitting a proximal face of the head to be substantially flush with the proximal face of the washer-type member when the screw-type member and the washer-type member are engaged.

8. The system recited in claim 5, wherein the washer-type member has a generally oval shape in axial cross section having two wings, a pair of barbs extending from each wing.

9. The system recited in claim 5, wherein the head has a generally circular shape in axial cross section and means for being driven by a driver.

10. The system recited in claim 9, wherein the screw-type member has a bore extending from the proximal end, the bore noncircular in axial cross section for permitting a driver to pass into the bore and to advance the screw-type member by being rotated in a direction having a handedness commensurate with the distal portion.

11. The system recited in claim 10, wherein the screw-type member bore extends axially through to a distal end for admitting an elongated driver thereinto.

12. The system recited in claim 5, wherein the extracting means comprises an elongated flexible member engageable with the washer-type member.

13. The system recited in claim 12, wherein the washer-type member has a second and a third hole therethrough from the proximal face to the distal face, the second and the third holes each dimensioned to permit the flexible member to pass therethrough for engagement therebetween, a first end of the flexible member passable through the second hole to emerge from the proximal face of the washer-type member, a second end of the flexible member passable through the third hole to emerge from the proximal face of the washer-type member to create a noose therearound.

14. The system recited in claim 1, wherein the engaging means comprises means for reversibly locking the first and the second fixation member together.

15. A method for affixing a piece of soft tissue within a bone tunnel comprising the steps of:

positioning a piece of soft tissue so that a portion thereof resides within a bone tunnel;

positioning a first fixation member against the piece of soft tissue within the bone tunnel;

engaging a second fixation member with a proximal portion of the first fixation member;

engaging a piece of the soft tissue outside the bone tunnel with an element on a distal face of the second fixation member;

disengaging the first fixation member from the soft tissue piece within the bone tunnel;

repositioning the soft tissue piece within the bone tunnel;

repositioning the first fixation member against the piece of soft tissue within the bone tunnel; and disengaging the second fixation member from the soft tissue piece and repositioning the second fixation member against a different piece of soft tissue outside the bone tunnel.

16. The method recited in claim 15, wherein the first fixation member positioning step comprises:

inserting a threaded distal portion of a screw-type member into the bone tunnel; and bearing a section of the threaded distal portion against a wall of the bone tunnel.

17. The method recited in claim 16, wherein:

the second fixation member engaging element comprises a barbed washer having a hole extending from a proximal face through to a distal face, the hole dimensioned for free rotation about the threaded distal portion of the screw-type member, a distal face of the washer having a plurality of barbs extending generally distalward; and the soft tissue engaging step comprises impaling the soft tissue piece outside the bone tunnel with the barbs.

18. The method recited in claim 17, wherein the disengaging step comprises the steps of:

attaching a flexible member to the washer; and pulling the flexible member until the barbs are removed from the soft tissue piece.

19. A system for affixing a piece of tissue to a bone comprising:

a generally cylindrical cannula adapted for insertion into a surgical site adjacent a tunnel in the bone;

a generally cylindrical screw dimensioned for insertion through the cannula member, the screw having a head at a proximal end and a threaded distal portion;

a barbed washer having a hole extending from a proximal face through to a distal face, the hole dimensioned for free rotation about the screw distal portion and for retention by the screw head therebeneath, the distal face having a plurality of barbs extending generally distalward for engaging and retraining a movement of the proximal tissue piece; and an elongated flexible member engageable with the washer for pulling the washer away from the proximal tissue piece if desired.

20. A method for affixing a piece of soft tissue into a bone tunnel comprising the steps of:

positioning a piece of soft tissue with a first portion within a bone tunnel and a second portion extending therefrom;

inserting a cannula into a surgical site with a distal end positioned adjacent a bone tunnel and against the soft tissue second portion;

inserting a screw having a head and a threaded distal portion through a hole in a washer having distally protruding barbs extending therefrom, the washer dimensioned for axial retention by the screw head and for rotational freedom of motion about the screw distal portion;

inserting the screw and washer assemblage into the cannula;

driving the screw into the bone tunnel and against the soft tissue, the washer permitted to spin against the screw while being retained within the cannula proximal portion;

permitting the barbs to bear against the soft tissue second portion adjacent the tunnel;

repositioning the washer and soft tissue second portion and permitting the barbs to bear against another section of the soft tissue second portion; and removing the cannula from the surgical site.

* * * * *